United States Patent [19]

Fowler et al.

[11] Patent Number: 5,124,554
[45] Date of Patent: Jun. 23, 1992

[54] EXPLOSIVES DETECTOR

[75] Inventors: Peter H. Fowler; Peter A. E. Stewart, both of Bristol, England; John D. Rogers, Chepstow, Great Britain; Martin J. Allen, Bristol, England

[73] Assignee: Rolls-Royce and Associates Limited, Derby, England

[21] Appl. No.: 656,942

[22] Filed: Feb. 19, 1991

[30] Foreign Application Priority Data

Feb. 20, 1990 [GB] United Kingdom ............. 9003851.4
Feb. 14, 1991 [GB] United Kingdom ............. 9103100.5

[51] Int. Cl.$^5$ .................... G01N 23/00; G01N 23/05
[52] U.S. Cl. ........................... 250/358.1; 250/390.02; 250/390.04; 376/159
[58] Field of Search ........... 250/358.1, 390.02, 390.04, 250/390.07, 359.1; 376/159

[56] References Cited

U.S. PATENT DOCUMENTS

| | | | |
|---|---|---|---|
| 3,832,545 | 8/1974 | Bartko | 250/390.04 X |
| 4,851,687 | 7/1989 | Ettinger et al. | 250/390.04 |
| 4,864,142 | 9/1989 | Gomberg | 250/390.04 |

FOREIGN PATENT DOCUMENTS

| | | |
|---|---|---|
| 0295429 | 12/1988 | European Pat. Off. |
| 0297249 | 1/1989 | European Pat. Off. |
| 8702170 | 3/1988 | PCT Int'l Appl. |
| 1392169 | 4/1975 | United Kingdom |
| 2150737 | 7/1985 | United Kingdom |
| 2151837 | 7/1985 | United Kingdom |
| 2217009 | 10/1989 | United Kingdom |

OTHER PUBLICATIONS

Foster et al., "Method for Measuring Total Cross Sections with Neutrons Having Energies from 2.5 MeV to 15 MeV", Nuclear Instruments & Methods 36, pp. 1-12.
Gonazi et al., "Explosive Detection System Based on Thermal Neutron Activation", IEEE AES Magazine, Dec. 1989, pp. 17-20.
Swinth, Conference, Proceedings of the Society of Photo Optical Instrumentation; Engineers Seminar on Imaging Techniques for Testing and Inspection, Los Angeles, Cailf. 1972, pp. 23-30.
"Neutrons Give Ray of Hope in Halting Plastic Explosive", the Sunday Times (London, England) 22 Jan. 1989.
"Neutron Detection for Kennedy", Flight International, 8 Jul. 1989.
"Airport Detectors not Ready for Terrorists", New Scientist, 26 Jan. 1991.

*Primary Examiner*—Constantine Hannaher
*Assistant Examiner*—Edward J. Glick
*Attorney, Agent, or Firm*—Oliff & Berridge

[57] ABSTRACT

Apparatus for non-invasively inspecting an object, such as an item of luggage, for explosives material comprises a multi-channel thermal neutron inspection system having a plurality of neutron irradiation chambers. Simultaneous operation of several channels increases maximum system throughout several times. Each chamber has a lithium neutron source which is stimulated to neutron production by a proton beam. Beam switching magnets are energized by pulsing to divert a common proton beam to each source in turn. The initial beam is generated by a radio frequency quadrupole accelerator. The advantages of this system are very low residual source activity and controllable neutron production thereby minimizing safety hazards. The irradiation chamber may contain several different gamma ray detectors to identify the presence elements present in explosives material. In addition a neutron radiography imaging means may be employed to identify the presence of potential shielding materials.

17 Claims, 5 Drawing Sheets

EXPLOSIVES DETECTOR

BACKGROUND OF THE INVENTION

1. Field of the Invention

The invention relates to explosive detectors. In particular the invention relates to a nuclear technique for monitoring objects such as luggage and parcel items and to screen such items for the presence of explosives materials.

The invention concerns a non-invasive method of inspection which involves subjecting the items to a thermal neutron environment and observing the gamma capture reaction.

It is an object of the present invention to provide a method and apparatus for non-invasively inspecting luggage by detecting gamma radiation emitted by selected elements in response to neutron irradiation.

The invention also has for an objective to positively detect the presence of explosives material by identifying certain characteristic elements. Further objectives include to pre-empt countermeasures which might be taken to conceal the explosives material, e.g. shielding; and to minimise false alarms while ensuring that quantities of material above a predetermined minimum do not go undetected.

Still further objectives of the system design include minimum system weight and minimum occupied floor area for the inspection system, source shielding and the baggage handling system. The baggage handling system is also intended to be capable of reaching a throughput of at least 10 bags/minute per channel in a multi-channel facility.

2. Description of the Prior Art

There are already in existence several types of non-invasive baggage inspection systems. The most familiar to air travellers is the ubiquitous x-ray apparatus. This type relies entirely on the visual skills and vigilance of human operators to spot suspicious objects. The systems have no inherent capability to detect explosives material itself.

There are a number of other systems designed to sense explosives material but each has perceived drawbacks which the present arrangements seek to either avoid altogether or to improve upon. The systems considered most effective use neutrons as the inspection medium. Of these there are three types of source each of which gives rise to a characteristic problem specifically addressed by the present invention.

In a first of these systems neutrons are produced by a deuterium-tritium reaction which takes place inside a containment vessel, generally referred to as a "reaction tube". These "tubes" are expensive to replace. Although the source is controllable the major drawback stems from the energy of the reaction which produces neutrons in a narrow energy band at 14 MeV only. These neutrons are too fast for the purpose and have to be moderated. At such energies shielding has to be very bulky.

A second type of system uses a continuous source, for example a californium isotope $Cf^{252}$. This produces neutrons having a useful spread of energies in the range 0.5–14 MeV with a mean about 2 MeV. Unfortunately it is a continuously radio-active source. This is undesirable from a security standpoint. The source is effectively uncontrolled, and because of the high energy of the neutrons requires bulky shielding.

The third type of source, also controllable, comprises a radio frequency quadrupole accelerator, which will be subsequently referred to as an RFQ accelerator. This impinges a beam of deuterons onto a beryllium target. It generates a reasonably monoenergetic neutron beam at about 7 MeV. The neutrons are still more energetic than required so a considerable degree of shielding and moderation is still necessary.

The advantages of the present invention which will be apparent from the subsequent description. The neutrons produced are low energy reducing shielding requirements. Other advantages includes easy source control, and the neutron source has only low and soft residual radioactivity. Also a high neutron flux at low proton current allows multi-channel inspection to raise total system throughput.

SUMMARY OF THE INVENTION

According to the broadest aspect of the present invention a method of detecting the presence of explosives material in an item under investigation includes the steps of exposing the said item to an environment of thermal neutrons and detecting gamma rays characteristic of selected elements.

Preferably the selected elements are nitrogen, carbon and hydrogen in any combination thereof.

According to one aspect of the invention there is provided apparatus for detecting explosives material in an item comprising:

a structure having walls defining an irradiation chamber for receiving the item, means for producing a beam of mixed energy neutrons including a lithium target, a source of protons and means for accelerating the protons in the direction of the target to produce said neutrons, means for producing a uniform distribution of thermal neutrons within the item, gamma ray detecting means disposed adjacent the irradiation chamber to detect gamma rays emitted as result of irradiation and to produce an output indicative of the energy of a detected gamma ray, and means for collating a plurality of said outputs to detect peaks in a gamma ray energy spectrum indicative of the presence of a predetermined element or elements in said item.

The uniform distribution of neutrons in the target volume is achieved by permitting a fraction of primary energy neutrons from the source, i.e. unmodulated, to travel directly to the item and a further substantial proportion to reach the target by reflection. Neutron capture takes place in the energy range 10 mev up to 100 mev (milli-electron volts). To ensure good penetration and uniform distribution a proportion of the neutrons are moderated to this level within the item. Others are slowed outside the item so they reach a thermal energy level at or close to the surface of the item. Lithium is a most suitable target material for achieving this because it possesses a high yield of neutrons in an advantageous primary energy range.

Preferably the apparatus comprises a plurality of irradiation chambers each of which is provided with a lithium target, and a beam of protons from a single proton source is selectively switched to each target as required.

According to another aspect of the invention the means for producing the neutrons comprises a source of protons, means for accelerating the protons towards a target, a lithium target arranged to emit neutrons into the irradiation chamber in response to protons impinging on the target.

Preferably the means for accelerating the protons comprises a radio frequency quadrupole accelerator. Also, the irradiation chamber is preferably at least partially surrounded by neutron reflecting means arranged to reflect neutrons towards the item whereby to produce a substantially uniform distribution of neutrons within the item.

BRIEF DESCRIPTION OF THE DRAWINGS

The invention and how it may be carried into practice will now be described in greater detail with reference to an example illustrated in the accompanying drawings, in which.

DETAILED DESCRIPTION OF THE PREFERRED EMBODIMENTS

Figure 1:
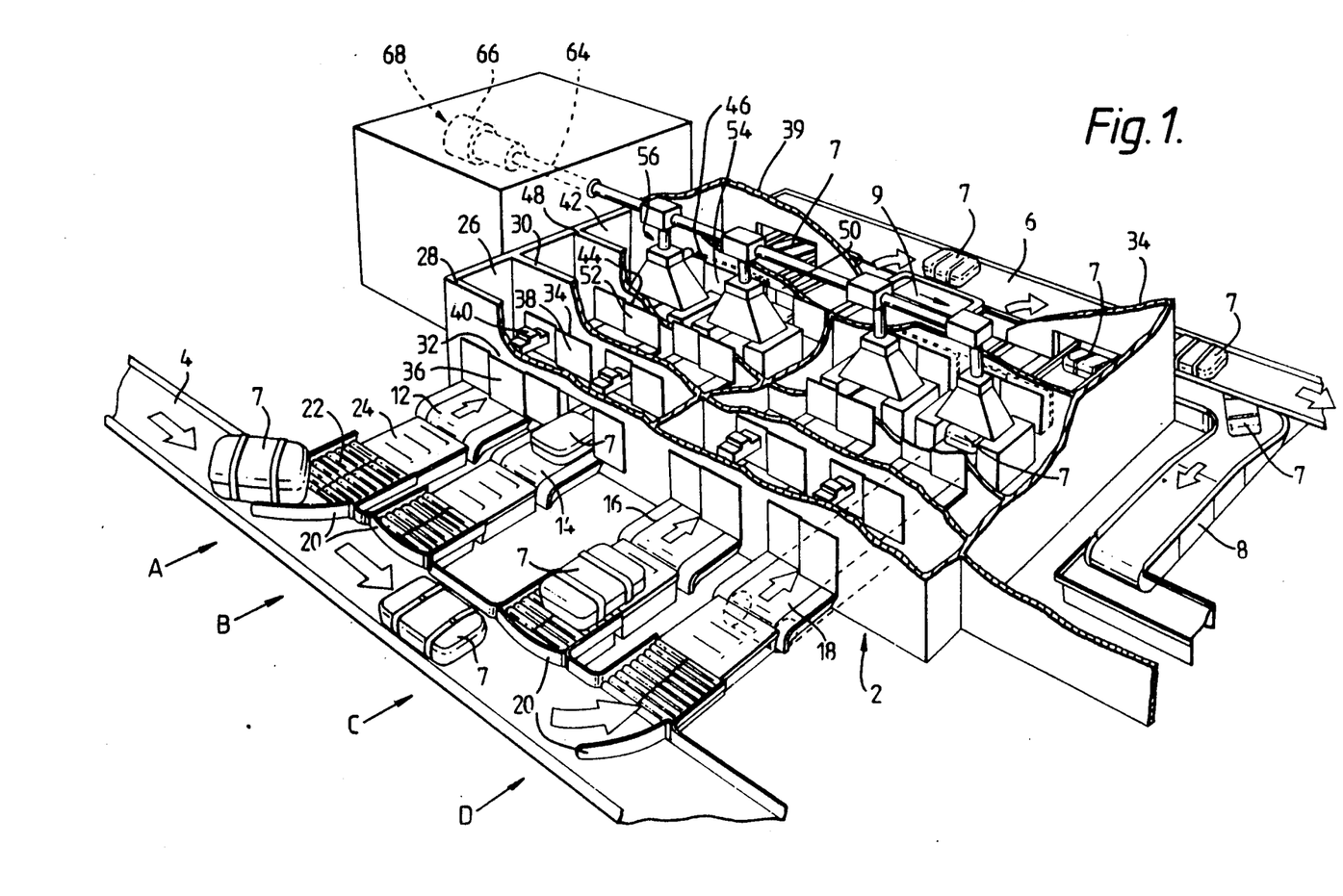
FIG. 1 is an overall perspective of a non-invasive luggage inspection system partly cutaway to reveal internal features.

FIG. 1 illustrates a non-invasive inspection system of the type that may be installed in airports to screen luggage for explosives material. The inspection equipment is housed within a shielding enclosure 2, to be described more fully below. Baggage is carried towards the enclosure 2 in a conveyer system 4 and is similarly carried away from it by one of two further conveyors 6 and 8. An item is delivered to one or other of the conveyors 6 or 8 according to its inspection results. Items on conveyor 6 have passed inspection and may be stowed ready for travel. Those which fail inspection are re-routed by a drop-down gate 9 to conveyor 8. Conveyor 8 delivers these to a designated location where they can be examined more closely.

The inspection equipment is a multi-channel system served by one radio frequency quadrupole accelerator. Hereinafter radio frequency quadrupole will be referred to by its initials RFQ. The illustrated equipment has four channels A, B, C and D. A greater or lesser number of inspection channels may be employed according to the required throughput. An item of incoming baggage is carried by a horizontal conveyor 4 through the inspection chamber 10 on one of four conveyor systems 12, 14, 16, 18. Individual items are selected for each channel merely on the basis of a conveyor vacancy.

The inspection conveyors 12–18 are disposed at right angles to the main conveyor 4. Each receives an item of luggage through a capture gate such as at 20. The other channels all have identical equipment. For the sake of brevity and clarity only one channel is referenced in the drawings and will be described here.

Capture gate 20 is swung open and across conveyor 4 to entrain an item of baggage when its associated inspection chamber is vacant. A captured item first passes onto a set of rollers 22 and then to an automatic weighing platform 24. After capture has been made the gate swings shut behind the item. Further items then pass onward to the next or a subsequent channel, or are recycled if all channels are temporarily full.

In FIG. 1, channel A is shown in the process of capturing an item. Channel D is ready to receive another item with its capture gate open. A previous suitcase has passed into a second inspection chamber. Chamber C has just captured a bag which is being loaded onto the automatic weighing platform 24. Its capture gate is closed. Meanwhile in channel B a suitcase is seen entering a first inspection chamber.

The inspection apparatus is housed wholly within the walls of shielding enclosure 2. From the automatic weighing platform 24 the circulating belt of conveyor 12 carries the luggage item to a first x-ray inspection chamber 26. The first chamber 26 is defined front and back, in the direction of luggage travel, by the external front wall 28 of the enclosure 2 and an internal dividing wall 30. Access openings 32, 34 formed in these walls through which the conveyor passes. Radiation proof shutters 36, 38 close these openings respectively, opening only to pass baggage items into the front and out through the rear wall of the chamber. At the rear of the structure an external back wall 39 is spaced from the rear of the radiography chamber to form a safe exit chamber. Baggage items pass through further access openings closed by radiation shutters, operation of which is synchronised to prevent direct line of sight into the neutron irradiation chamber.

A conventional x-ray radiography unit 40 is positioned in the roof of the first chamber directed downwards towards the conveyor. When activated this x-ray unit will produce an x-ray image of any item positioned beneath it. Operation of the x-ray unit 40 is synchronised with the shutters and the conveyor. In the particular example being described x-ray units for adjacent channels, e.g. A and B, C and D, are located in a common inspection chamber. Thus adjacent conveyors 12 and 14, also 16 and 18, feed luggage into common inspection chambers. However, these inspection chambers may, if preferred, contain only a single x-ray unit. Other multiple groupings are also possible where suitable.

After x-ray the baggage item is moved from the first, x-ray inspection chamber 26 into a second, neutron radiography chamber 42. Luggage enters and leaves this second chamber through access openings 44, 46 in front and rear walls 48, 50 respectively. As before openings 44, 46 are normally closed by radiation proof shutters 52, 54. Operation of the shutters is synchronised with movement of the luggage conveyor 12 together with energisation of neutron radiography unit. The neutron radiography unit is indicated generally at 56 in FIG. 1 and will be described in greater detail with reference to FIG. 2.

Figure 2:
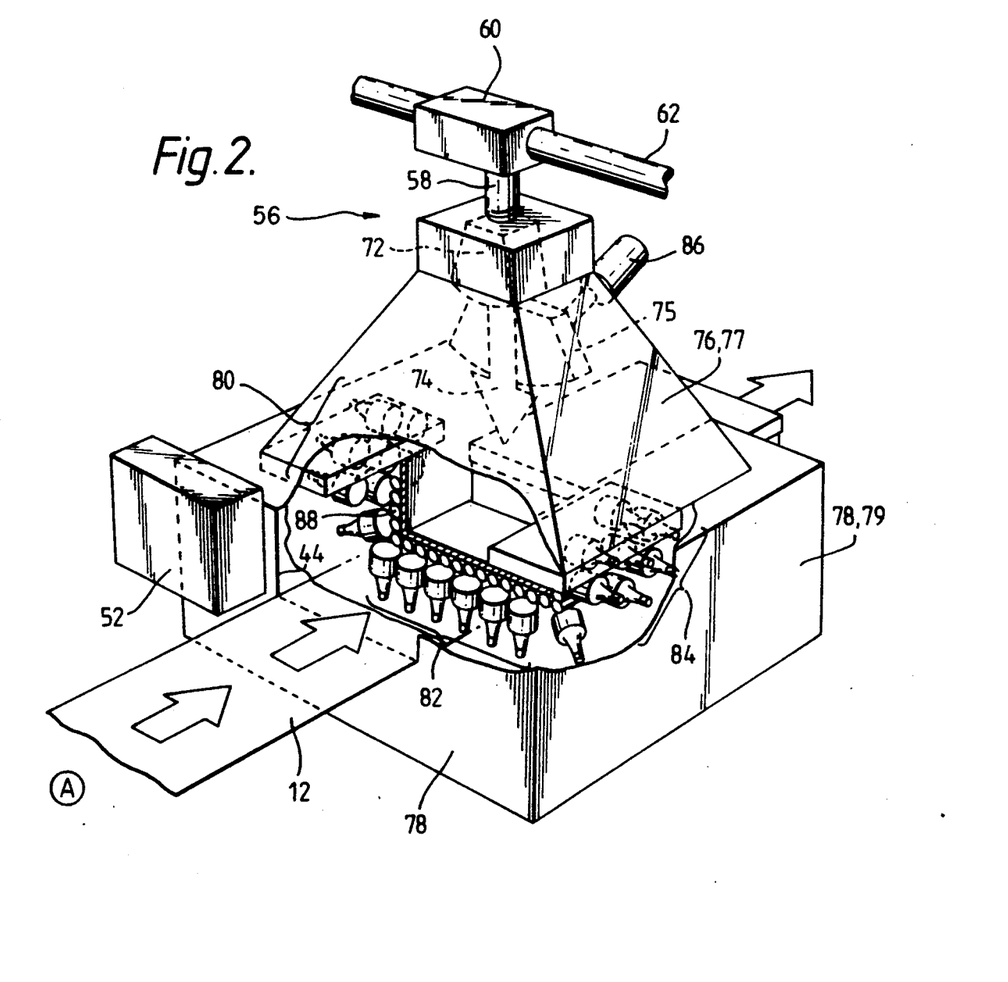
FIG. 2 is an enlarged view of a portion of FIG. 1 showing a neutron source and irradiation chamber in more detail.

Each neutron radiography unit 56 includes a neutron source comprising a lithium target upon which protons are made to impinge. The unit 56 is located in the uppermost part of the inspection chamber 42. In this location it is disposed to direct neutrons towards the item undergoing inspection. Protons enter the unit via a short length of vertical beam tube 58 which passes through the roof and shielding of the chamber. Similarly to the x-ray units the neutron radiography units are housed in pairs within an inspection chamber. Preferably as shown in FIG. 2 the radiography units share the gamma-irradiation chamber. They may, however, be housed singly or in other multiples. The vertical beam tube 58 to each of the units receives protons from a common source. Each vertical tube 58 is connected with beam switching magnet 60 placed in line with a main beam tube 62. For four neutron radiography units in four channels A, B, C and D four beam switching magnets 60 are provided in the main beam tube 62. Each beam switching magnet 60 can selectively switch the proton beam into a beam tube 58 leading directly to a corresponding radiography unit 56.

A proton source and means for accelerating the protons is located at one end the main beam tube 62. The output beam tube 64 of an RFQ accelerator, generally indicated at 66, injects protons into the tube 62. The detailed construction and operation of the RFQ accelerator 66 is not part of the subject matter of the present invention. A more detailed description is available elsewhere in published literature if required. It will not be further explained here. In response to a pulsed electrical input at 68 the RFQ accelerator produces a pulse of 2.5 MeV protons along main beam tube 64. An appropriately synchronised control pulse to a selected beam switching magnet 60 will then switch the pulse of protons into the corresponding branch beam tube 58 to impinge on a neutron producing target.

Referring now to FIG. 2, the gamma-ray and neutron radiography unit 56 is shown in greater detail. Protons from switching magnet 60 travel down a short vertical beam tube 58 towards a lithium target 72. The consequential reaction produces a neutron flux of mixed energies generally directed in the downward direction. The angular distribution of this neutron flux is strongly peaked in the forward direction. The maximum energy of the produced neutrons is only 0.77 MeV (Mega-electron volts) with a mean energy of 0.5 MeV in the forward direction. Neutrons at wider angles have an average energy of only 0.3 MeV and are easily reflected or absorbed by surrounding shielding 76,78.

The target 72 includes a moderator 73 surrounding the source which reflects and absorbs wide angle neutrons. The surrounding shielding absorbs stray neutrons not travelling in the preferred direction towards the inspection volume. This, in combination with the strongly peaked angular distribution, allows about 50% of the neutrons produced to be emitted into the exposure volume. The neutron beam is indicated by the shaded arrow 74 in the drawing. The collision involved in each neutron reflection absorbs a proportion of the neutron's energy. As a result the average energy of the beam is progressively thermalised.

Immediately below the lithium source and in front of an aperture in the target shielding is placed a bismuth gamma shield 75 through which the beam 74 emerges. This shield absorbs high energy gamma rays emitted by the target which could damage, or at least impair the performance, of the gamma ray detectors below.

Figure 3:
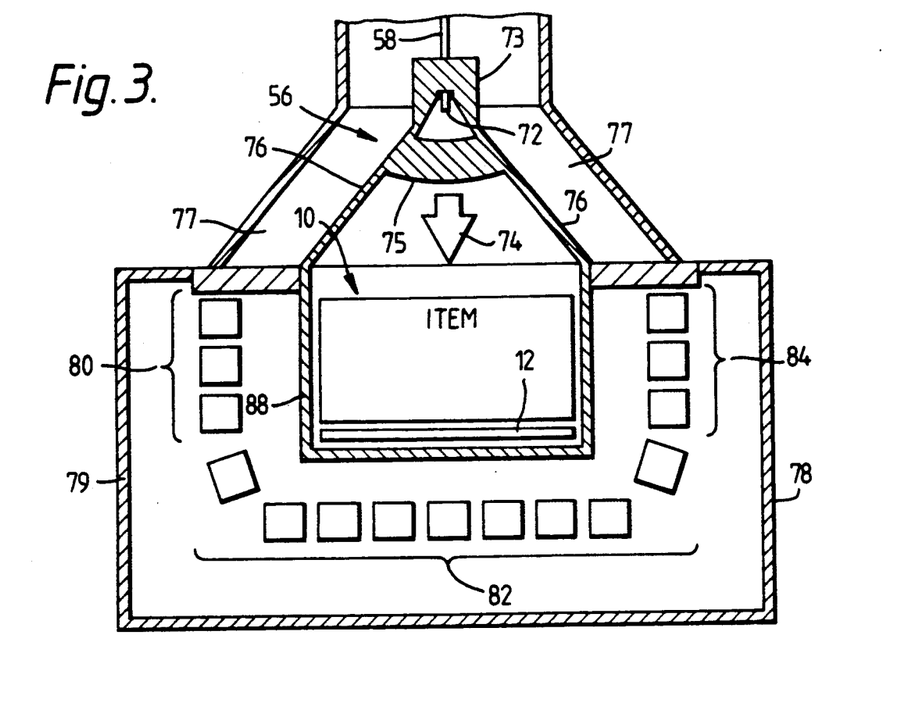
FIG. 3 shows a schematic diagram of a vertical section through the source and chamber of FIG. 2 viewed in the direction of travel of an item of baggage.
Figure 4:
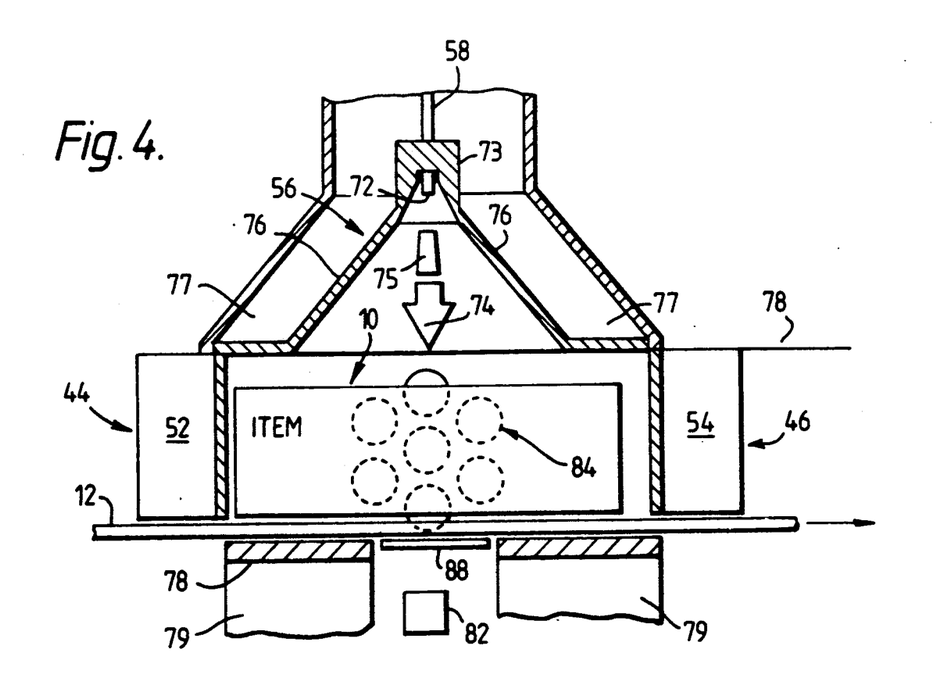
FIG. 4 shows a view corresponding to that of FIG. 3 from the side of the apparatus.

The irradiation volume where an item of baggage is irradiated is defined by surrounding reflectors 76,78 and shielding indicated at 77, 79 in FIGS. 2, 3 and 4. The circulating belt conveyor 12 passes through this volume.

It enters and exits the shielded volume through openings protected by movable radiation shutters, which have been omitted from FIG. 2 for clarity but which may be seen in FIGS. 1 and 4. As is clear from FIG. 4 the shutters 52, 54 incorporate reflectors and neutron shielding. In the side walls on either side of the conveyor and set into the floor beneath it are gamma detector arrays 80, 82 and 84.

The three sets of gamma ray detectors 80, 82 and 84 are arranged in a U-shaped array, the open side of the U-shape facing upwards towards the neutron source 72. Basically the detectors are arranged in a vertical plane, which contains the source or target 72 and which intersects the space through which the item being inspected is passed.

In the lowest of the three sets of detectors 82 the individual detectors are arranged in a linear array adjacent the lower surface of the inspected item. The gamma-ray detectors are protected from incident neutrons by sufficient neutron shielding, e.g. borated paraffin wax. The remaining detectors of sets 80 and 84 are arranged in two circular arrays facing each other across the inspection space. The item passes between these two arrays. See FIGS. 3 and 4 which shows views at right angles.

The gamma ray detectors contain inorganic scintillation material responsive to the incidence of gamma ray energy. The preferred material is sodium iodide.

However, other possible materials from which the detectors may be formed include barium flouride, bismuth germanate, etc. The selected detector material should not be susceptible to damage by neutrons. In the example being described a layer of shielding is placed in front of the detectors.

An additional high resolution gamma ray detection means is provided with an angle of view encompassing substantially the whole of the inspection space. A single germanium high resolution detector 86 is positioned in an upper part of the inspection chamber and inclined at an angle with respect to the inspection plane. High purity germanium is easily damaged by the fast neutrons in the beam. This detector is therefore positioned where it can be adequately shielded from the faster neutrons.

To achieve consistent detection with a high degree of confidence it is essential to have uniform distribution of neutrons in the right energy range throughout the volume of the item to be inspected with it in place. In the present arrangement this distribution is achieved by a combination of factors. The item is effectively placed in a "well" formed by the surrounding neutron reflecting walls. While it is in the "well" it is bathed in thermal neutrons. Some of the neutrons are thermalised inside the item largely by the normal hydrogen content of luggage. Others arrive from the reflecting/moderating walls already thermalised. Some of the neutrons arrive directly from the source, or after relatively few collisions, while others have been reflected numerous times. Within the item, therefore, the distribution neutrons is isotropic with a substantial energy range.

The most common stable isotope of nitrogen is $N^{14}$. The neutron capture reaction between the thermal neutrons and the bombarded nitrogen atoms produces $N^{15}$ · which emits gamma rays. About 15% of these capture reactions emit gamma-rays with a characteristic energy of 10.83 MeV. The spectrum of emitted gamma ray energy therefore exhibits a strong peak at 10.83 MeV. Other elements, including carbon and hydrogen, behave in a similar fashion and emit gamma rays with characteristic tell-tale peaks at other energies.

Figure 5:
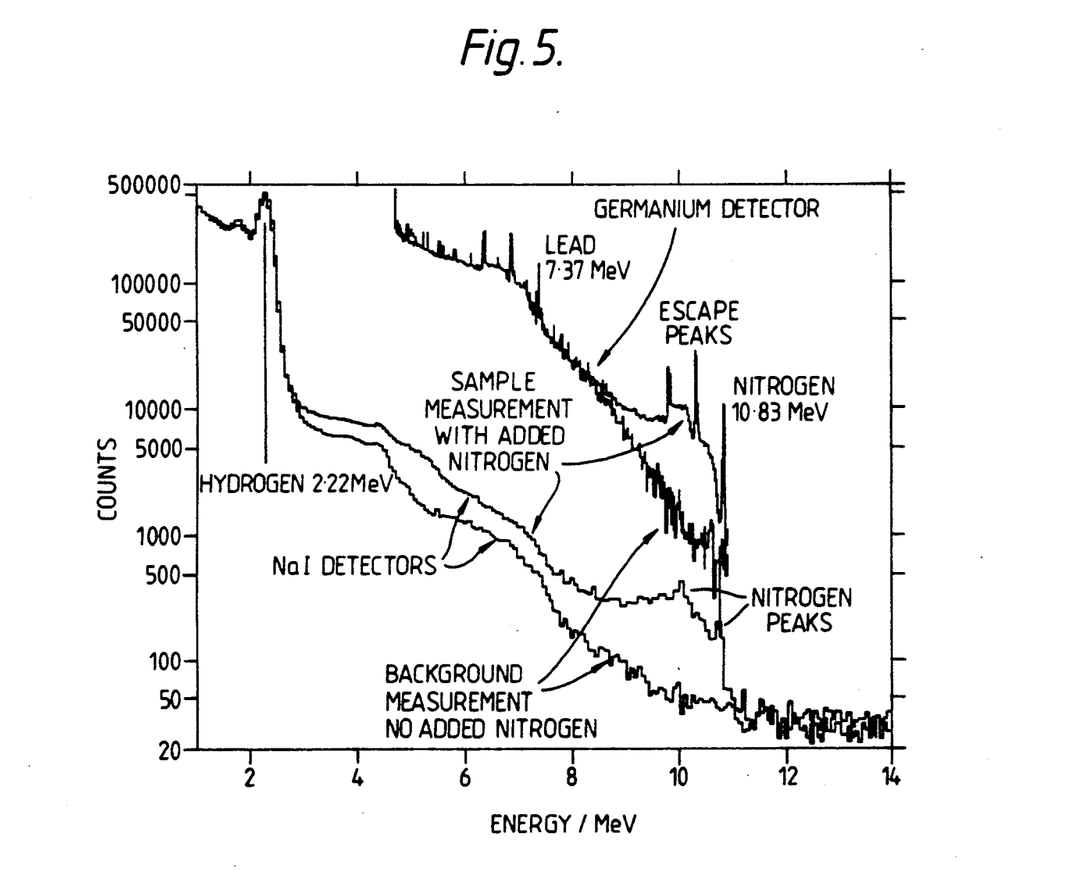
FIG. 5 shows a diagram plotted graphically of a gamma ray detector output.

The scintillation detectors in response to the incidence of a gamma ray produce an electrical output pulse the amplitude of which is proportional to the gamma ray energy. FIG. 5 shows in graphical form typical collated outputs from a sodium iodide detector and a germanium detector. It will be apparent that the sharper resolution of the germanium detector permits clear identification of gamma ray peaks due to its superior resolution. The main sodium iodide detectors being spaced along three sides of an item under inspection have useful positional sensitivity for nitrogen and other elements detected. This is inherent in the distribution with time of the appropriate gamma ray counts of individual detectors. The germanium detector is able to act as a general monitor and to identify suspicious peaks due to the presence of certain materials. For example, mercury is often present as mercury fulminate in detonators. Chlorine is the base of an alternative family of explosives which contain no nitrogen.

A further arrangement of detectors for carrying out neutron radiography is illustrated in FIGS. 2,3 and 4. This comprises a plurality of neutron detectors, one of which is indicated at 88. Such a detector essentially comprises a cylinder of metal which has a low neutron capture cross-section and which is filled with helium 3 (He3). The detection cylinders 88 are mounted with their cylindrical axes parallel with the direction of movement of the item and transverse to the general direction of incident neutrons, arrow 74. The detectors are also distributed in a U-shaped array on three sides of an object undergoing inspection. This U-shaped radiography detector array may be positioned beside the sodium iodide detectors or in front of them. Preferably, the array of neutron detectors is located immediately in front of the sodium iodide detectors.

The neutron detectors 88 yield a coarse image of the transparency of the item to neutrons. The image contains both transmitted and reflected neutrons. Blurring can be reduced by arranging collimation around each detector so that it responds only to near axis neutrons. The purpose of this detector array is to check for regions of the item which neutrons do not penetrate thereby revealing that neutron shielding has been employed. The use of neutron absorbers would be recognised immediately as suspicious and requiring further investigation. Gamma-rays from the neutron absorbing materials are also detected by the germanium detector 86.

Figure 6:
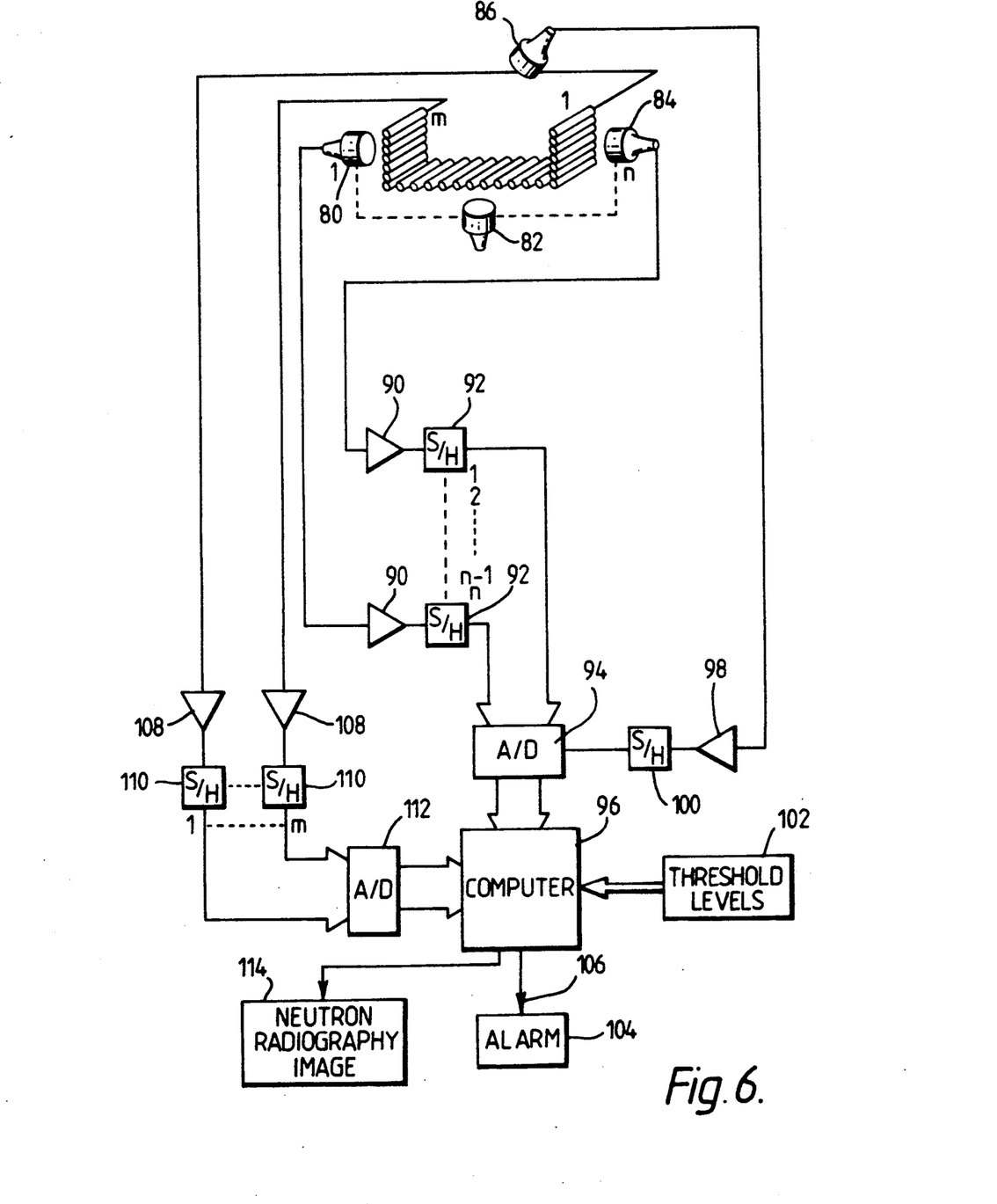
FIG. 6 shows a schematic diagram of the detector output signal processing system.

FIG. 6 illustrates a general signal processing system for the number of detector output signals produced in the system. Basically all signals are digitised and then processed by a computer. Power supplies and high voltage detector bias circuits are not illustrated in the drawing for clarity.

Referring first to the sodium iodide detectors of arrays 80,82,84 the output of each detector is passed via a pre-amp 90 to a sample and hold circuit 92. For clarity not all detector output signal leads are shown. Only the first and nth are indicated. The signal values held in circuits 92 are periodically read and digitised by analogue to digital convertor 94 and passed to a computer 96. As previously discussed the amplitude of these signals is indicative of gamma ray energy. Thus, by counting signals having amplitudes in discrete narrow bands an energy distribution spectrum is built-up, such as that shown as the lower curve in FIG. 5.

Signals from the single high resolution germanium detector 86 can be built-up in the same way. Its output is passed through pre-amp 98 and sample and hold circuit 100. In the example this signal is also sampled by A/D converter 94. Computer 96 notionally assembles a high resolution energy spectrum such as the upper curve of FIG. 5.

In FIG. 5 the characteristic peaks of nitrogen, at 10.83 MeV, and of hydrogen at 2.22 MeV can be clearly seen. Also the greater resolution of the germanium detector is evident in the nitrogen peak. Signals representing energy windows for specific gamma ray energies are stored in a read only memory 102 and compared by computer 96 with the counts at those energy levels in the energy spectrum derived for an inspection item. In the event one or more of the threshold levels is exceeded an alarm circuit 104 is energised. In addition, or alternatively to an audible alarm, other action may be taken. For example the alarm signal 106 may control reject gate 9 in FIG. 1. Thus, when a suspect item is identified the gate 9 may be lowered in synchronism with operation of the conveyor 12 to divert the item to reject conveyor 8 for a second level of inspection.

The output signals from the neutron radiography detectors 88 can be processed in substantially the same way. Again only the first and mth signal output lines are shown in the drawing. The signals are passed through pre-amps 108 and sample and hold circuits 110 to an analogue to digital converter 112. The computer 96 can then process the digital signals to provide a coarse radiography image on screen 114. This may be combined with or superimposed on an x-ray image of the item produced by x-ray apparatus 40.

The relatively modest shielding requirements of the arrangement described above will be readily appreciated in view of the lack of high energy neutrons. Conventional shielding materials may be employed such as borax or dense boron loaded polyethylene. Unfortunately this emits gamma-rays which will raise background levels adversely affecting system sensitivity. Lithium carbonate loaded polyethylene which produces greatly reduced gamma-ray emmissions is preferred. For the same reason a moderator containing heavy water (deuterium) is also preferred. The whole structure is surrounded by lead to absorb stray emissions. The conveyers which pass through the irradiation chambers are constructed of low gamma emitting material and low residual activity material.

The invention has been described with reference to the particular embodiment illustrated in the accompanying drawings. Nevertheless it should be understood that various adaptations and modifications may be made. The scope of the invention is limited only by the following claims.

We claim:

1. Apparatus for detecting explosives material in an item by means of a thermal neutron activation process comprising:

a structure having walls defining an irradiation chamber for receiving the item, neutron source means for producing a beam of mixed energy neutrons including:

a lithium target, a source of protons, a radio frequency quadropole accelerator (RFQ) means for accelerating the protons, the RFQ means being energized to accelerate the protons to an energy of 2.5 MeV in a direction of the lithium target whereby an endothermic reaction produces neutrons in a direction of an incident beam having a mean energy of 0.5 MeV and a peak energy of 0.77 MeV, means within the irradiation chamber for moderating and reflecting neutrons to produce a uniform distribution of thermal neutrons within the item placed within the irradiation chamber, gamma ray detecting means disposed adjacent the irradiation chamber to detect gamma rays emitted by contents of the item as a result of thermal neutron activation caused by said neutrons and to produce an output indicative of an energy spectrum of aid detected gamma rays, and means for collating a plurality of said outputs to detect a resonance in a gamma ray energy spectrum indicative of a presence of at least one predetermined element in said item.

2. Apparatus as claimed in claim 1 comprising a plurality of irradiation chambers each of which is provided with a lithium target, a beam of protons from a single proton source being selectively switched to each target as required.

3. Apparatus as claimed in claim 2 wherein the means for selectively switching the proton beam to a target comprises a beam switching magnet.

4. Apparatus as claimed in claim 1, wherein the gamma ray detecting means comprises a plurality of inorganic detectors disposed in a first plane containing the neutron source means and intersecting a volume in the irradiation chamber through which the item being inspected is passed.

5. Apparatus as claimed in claim 4 wherein the plurality of inorganic gamma ray detectors are arranged in a U-shaped array an open side of which faces towards the neutron source means.

6. Apparatus as claimed in claim 5 wherein side limbs of the U-shaped array of inorganic detectors contain a plurality of inorganic detectors disposed in circular arrays facing inwards towards the inspection volume.

7. Apparatus as claimed in claim 4 wherein the inorganic detectors for detecting gamma rays comprise sodium iodide.

8. Apparatus as claimed in claim 4 further comprising additional gamma ray detecting means of more sensitive type disposed in a second plane inclined with respect to the first plane.

9. Apparatus as claimed in claim 8 wherein said additional gamma ray detecting means is positioned to avoid impingement by neutrons in the inspection beam.

10. Apparatus as claimed in claim 8 wherein the additional gamma ray detecting means comprises germanium.

11. Apparatus as claimed in claim 11 further comprising neutron detecting means directly responsive to the impingement of neutrons disposed relative to the irradiation chamber to detect a neutron capture profile of an inspected object.

12. Apparatus as claimed in claim 11 wherein the neutron detecting means comprises a plurality of neutron detectors disposed in a U-shaped array an open side of which faces towards the neutron source means.

13. Apparatus as claimed in claim 12 wherein the U-shaped array of neutron detectors is disposed inside a U-shaped array of gamma ray detectors.

14. Apparatus as claimed in claim 11 wherein the neutron detectors comprise cylinders of metal having a low neutron capture cross-section and filled with helium 3 (He3).

15. Apparatus as claimed in claim 1 wherein the means for collating the plurality of said outputs includes means for collating the plurality of said outputs to form a gamma ray energy spectrum, means for storing said energy spectrum and means responsive to said stored energy spectrum to compare an amplitude of peaks formed in the energy spectrum with predetermined threshold limits to determine a presence of designated elements corresponding to said peaks.

16. Apparatus as claimed in claim 15 further comprising alarm means responsive to positive detection of the designated elements to warn of their detection.

17. Apparatus as claimed in claim 1 further comprising means for passing the object to undergo inspection through the irradiation chamber in order to produce detector signals in respect to the whole volume of the object.

* * * * *